United States Patent [19]

Jakobson et al.

[11] Patent Number: 5,424,469
[45] Date of Patent: Jun. 13, 1995

[54] PROCESS FOR PREPARING POLYGLYCEROL FATTY ACID ESTER MIXTURES AND USE IN COSMETIC, PHARMECEUTICAL AND CHEMICAL PREPARATIONS

[75] Inventors: Gerald Jakobson; Werner Siemanowski, both of Rheinberg; Karl-Heinz Uhlig, Krefeld-Traar, all of Germany

[73] Assignee: Solvay Fluor und Derivate GmbH, Hannover, Germany

[21] Appl. No.: 89,820

[22] Filed: Jul. 12, 1993

[30] Foreign Application Priority Data

Jul. 16, 1992 [DE] Germany ............. 42 23 407.7

[51] Int. Cl.$^6$ .................. C07C 69/30; C11C 3/02
[52] U.S. Cl. ................... 554/227; 554/168; 554/170; 554/172; 424/401; 252/581
[58] Field of Search ................ 559/173, 168, 172; 424/401; 252/581

[56] References Cited

U.S. PATENT DOCUMENTS

| | | | |
|---|---|---|---|
| 5,045,337 | 9/1991 | El-Nokaly et al. | 426/602 |
| 5,130,056 | 7/1992 | Jakobson et al. | 252/551 |
| 5,147,644 | 9/1992 | Oppenlaender | 424/401 |
| 5,247,114 | 9/1993 | Jakobson et al. | 554/227 |

FOREIGN PATENT DOCUMENTS

| | | |
|---|---|---|
| 289636 | 11/1988 | European Pat. Off. |
| 451461 | 10/1991 | European Pat. Off. |
| 499700 | 8/1992 | European Pat. Off. |
| 3902374 | 8/1990 | Germany |
| 4005819 | 8/1991 | Germany |
| 3081252 | 4/1991 | Japan |
| 4145046 | 5/1992 | Japan |

*Primary Examiner*—José G. Dees
*Assistant Examiner*—Deborah D. Carr
*Attorney, Agent, or Firm*—Evenson, McKeown, Edwards & Lenahan

[57] ABSTRACT

A process for preparing polyglycerol fatty acid ester mixtures in which a polyglycerol mixture of 0.1 to 20 wt % monoglycerol, 20 to 35 wt % diglycerol, 30 to 40 wt % triglycerol and 49.9 to 5 wt % tetra- and higher polyglycerols is reacted with one or more fatty acids, selected from the saturated $C_8$- to $C_{18}$-fatty acids (containing 0 to 15 wt % unsaturated fatty acids), in a molar ratio of the polyglycerol to the fatty acid component of 0.3:1.5 to 1.5:0.5 in the presence of at least one catalyst and at reduced pressure, by initially heating the reaction mixture to at least 140° C. and reducing the pressure to at least 600 mbar and then heating the reaction mixture at a temperature from 140° to 220° C. and reducing the pressure from 600 to 10 mbar. After completion of the reaction, the resulting polyglycerol fatty acid ester mixture is cooled and optionally worked up and/or purified. Also disclosed are polyglycerol fatty acid ester mixtures prepared by the process, a liquid thickening agent, an oil/water emulsifier, and the use of the polyglycerol fatty acid ester mixture in pharmaceutical, cosmetic and other chemical preparations.

41 Claims, No Drawings

PROCESS FOR PREPARING POLYGLYCEROL FATTY ACID ESTER MIXTURES AND USE IN COSMETIC, PHARMECEUTICAL AND CHEMICAL PREPARATIONS

BACKGROUND OF THE INVENTION

The present invention relates to a process for preparing polyglycerol fatty acid ester mixtures from a $C_8$- to $C_{24}$-fatty acid and a polyglycerol mixture containing 0 to 5% by weight of monoglycerol, 15 to 40% by weight of diglycerol, 30 to 55% by weight of triglycerol, 10 to 25% by weight of tetraglycerol and 0 to 30% by weight of higher polyglycerols with acidic catalysis.

The invention furthermore relates to polyglycerol fatty acid ester mixtures, thickening agents and oil/water emulsifiers prepared by the process and having a very specific composition with respect to the polyglycerol employed, the fatty acids used and the degree of esterification, and to the use of polyglycerol fatty acid ester mixtures of this type.

The main industrial production of polyglycerol fatty acid ester mixtures is based on the direct esterification of fatty acids with polyglycerols of various chain lengths which are designated as a polyglycerol mixture or simply as polyglycerol) in the presence of an alkaline catalyst at elevated temperature. The known processes, however, are not selective, so that mixtures of undefined esters of polyglycerols with saturated and unsaturated fatty acids are obtained. The preparation of polyglycerol fatty acid esters of defined composition necessitates a complicated reaction sequence (in general introduction of protective groups into the polyglycerol compounds is necessary), and the reaction conditions are difficult to control.

The use of mixtures of polyglycerol fatty acid esters as emulsifiers in cosmetic and pharmaceutical preparations is disclosed in Published German Patent Application No. DE 4,005,819, the polyglycerol fatty acid ester mixture being prepared by partial esterification of polyglycerol mixtures of 0 to 5% by weight of monoglycerol, 15 to 40% by weight of diglycerol, 30 to 55% by weight of triglycerol, 10 to 25% by weight of tetraglycerol and 0 to 30% by weight of higher polyglycerols with at least one unsaturated fatty acid having 16 to 22 carbon atoms. Partial esterification of the polyglycerols occurs, but only an undefined mixture of polyglycerol fatty acid esters having a general degree of esterification of between 20 and 70% is obtained. The teachings of this document do not enable preparation of polyglycerol fatty acid ester mixtures having a specific composition and distribution of the esters in the mixture.

Published German Patent Application No. DE 3,902,374 discloses a detergent, cleaning agent and/or body shampoo which, in addition to an ionic and/or amphoteric surfactant, contains $C_8$ to $C_{18}$ fatty acid monoesters of diglycerol and/or $C_8$ to $C_{18}$ fatty acid diesters of tetraglycerol. This composition is characterized by good processability and skin compatibility and is readily biodegradable. However, it has the disadvantage that a relatively expensive and energy-consuming multi-step process is required for its preparation. It also has the disadvantage that it is normally obtained as a solid product, which leads to difficulties during further processing, e.g. into preparations etc., because it cannot be pumped at room temperature. There is also a risk of blockage of supply and metering devices. To dissolve the product it is necessary to apply heat and/or strong shear forces.

European Patent Application No. EP-A 0,289,636 discloses an emulsified or solubilized sterol composition in which the sterols are emulsified or solubilized in an aqueous solution of a polyhydroxy compound or in a liquid polyhydroxy compound which contains sucrose and/or polyglycerol fatty acid esters. The polyglycerol fatty acid esters which act as solubilizers and emulsifiers are obtained by esterification of polyglycerols having a degree of polymerization of 4 to 10 and saturated and/or unsaturated fatty acids containing 10 to 24 carbon atoms, the content of monoesters being at least 50% by weight.

Despite all the activity of the prior art, there remained a need for polyglycerol fatty acid ester mixtures having a defined composition and improved properties and handling and for an economical process for preparing such polyglycerol fatty acid ester mixtures.

SUMMARY OF THE INVENTION

It is the object of the present invention to provide a process for preparing polyglycerol fatty acid ester mixtures having a defined composition.

Another object of the invention is to provide a process for preparing polyglycerol fatty acid ester mixtures using a simple and economical reaction procedure.

A further object of the invention is to provide a process for preparing polyglycerol fatty acid ester mixtures which have a constant and reproducible composition.

It is also an object of the present invention to provide a polyglycerol fatty acid ester mixture which is liquid at room temperature so that it can be easily processed and mixed with other materials.

An additional object of the invention is to provide a polyglycerol fatty acid ester mixture which has thickening, oil-restoring and/or skin-care properties.

Yet another object of the invention is to provide a polyglycerol fatty acid ester mixture which can be used as an emulsifier and/or solubilizing agent in a wide variety of applications, including cosmetics, pharmaceuticals, detergents and cleaners, etc.

A still further object of the invention is to provide a polyglycerol fatty acid ester mixture which is non-toxic and ecologically acceptable.

These and other objects of the invention are achieved by providing a process for preparing a polyglycerol fatty acid ester mixture from a $C_8$- to $C_{24}$-fatty acid and a polyglycerol mixture containing 0 to 5 wt % monoglycerol, 15 to 40 wt % diglycerol, 30 to 55 wt % triglycerol, 10 to 25 wt % tetraglycerol, and 0 to 30 wt % higher polyglycerols with acidic catalysis, the process comprising reacting a polyglycerol comprising (relative to 100 parts by weight of polyglycerol):

0.1 to 20 wt % monoglycerol,
20 to 35 wt % diglycerol,
30 to 40 wt % triglycerol, and
49.9 to 5 wt % tetra- and higher polyglycerols, with at least one fatty acid selected from the group consisting of saturated $C_8$- to $C_{18}$-fatty acids, the at least one fatty acid containing from 0 to 15 wt % unsaturated fatty acids, in a molar ratio of polyglycerol to the at least one fatty acid of from 0.3:1.5 to 1.5:0.5, in the presence of at least one catalyst and at reduced pressure, the reacting step being carried out by:

initially heating the fatty acid and polyglycerol mixture to a temperature of at least 140° C. and reducing the pressure to 600 mbar;

subsequently heating the mixture in a temperature range from 140° to 220° C. under control of a temperature program and simultaneously reducing the pressure under control of a pressure program from 600 to 10 mbar;

removing water of reaction by continuous distillation; and upon attaining an acid number of less than 3, cooling the resulting polyglycerol fatty acid ester mixture.

In accordance with further aspects of the invention, the objects are achieved by providing a polyglycerol fatty acid ester mixture prepared by reacting a polyglycerol with at least one fatty acid selected from the group consisting of saturated $C_8$- to $C_{18}$-fatty acids containing 0 to 15 wt % of unsaturated fatty acids at elevated temperature, the polyglycerol fatty acid ester mixture (A) comprising:

0.1 to 20 parts by weight monoglycerol fatty acid ester, 20 to 35 parts by weight diglycerol fatty acid ester, 30 to 40 parts by weight triglycerol fatty acid ester, and 49.9 to 5 parts by weight tetra- and higher polyglycerol fatty acid esters, for a total of 100 parts by weight;

(B) having a degree of esterification of 20 to 80 wt % of fatty acid monoesters, and 80 to 20 wt % of fatty acid diesters containing 0 to 15 wt % of tri- and higher esters, and (C) containing 0 to less than 5 wt % free polyglycerol.

DETAILED DESCRIPTION OF PREFERRED EMBODIMENTS

The invention thus relates to a process of reacting a polyglycerol with at least one fatty acid which is characterized in that the polyglycerol, which consists (relative to 100 parts by weight of polyglycerol) of 0.1 to 20% by weight of monoglycerol, 20 to 35% by weight of diglycerol, 30 to 40% by weight of triglycerol and 49.9 to 5% by weight of tetra- and higher polyglycerols is reacted with one or more fatty acids, selected from the saturated $C_8$- to $C_{18}$-fatty acids, the fatty acid or the fatty acid mixture having a content of 0 to 15% by weight of unsaturated fatty acids, in a molar ratio of the polyglycerol to the fatty acid or to the fatty acid mixture of 0.3:1.5 to 1.5:0.5, preferably 0.5:1 to 1.2:1, in the presence of at least one catalyst, preferably an acidic catalyst, and at reduced pressure, by initially heating the reaction mixture to 140° C., preferably 145° C., and reducing the pressure to 600 mbar, preferably 500 mbar, and then heating the reaction mixture in a temperature range from 140° to 220° C., preferably
145° to 190° C., stepwise or continuously, controlled by means of a temperature program, and at the same time reducing the pressure, stepwise or continuously, controlled by means of a pressure program, from 600 to 10 mbar, preferably
from 500 to 20 mbar, the resultant water of reaction being continuously removed by distillation and on attaining an acid number of <3, the resulting polyglycerol fatty acid ester mixture being cooled and optionally worked up and/or purified for particular applications.

According to a preferred embodiment of the process according to the invention, a polyglycerol mixture is employed which consists (relative to 100 parts by weight of polyglycerol) of 6 to 16% by weight of monoglycerol, 23 to 33% by weight of diglycerol, 31 to 37% by weight of triglycerol and 40 to 14% by weight of tetra- and higher polyglycerols or contains these constituents.

Surprisingly, it was found in this process that the addition of glycerol in the claimed amounts according to the invention brings about an improvement in the solubility of the appropriate polyglycerol fatty acid ester mixture in aqueous formulations.

According to a preferred embodiment of the process of to the invention, which is advantageous or necessary for certain applications, the obtained polyglycerol fatty acid ester mixture is purified and/or worked up in order to remove unreacted polyglycerol from the product.

To do this, the polyglycerol fatty acid ester mixture obtained by the process according to the invention is cooled to 30° to 110° C., preferably 60° to 80° C., and subsequently subjected to an extraction treatment by treating the polyglycerol fatty acid ester mixture with an organic chemical solvent or solvent mixture and then extracting with water in at least one extraction step, an amount by weight of an inorganic and/or organic, basic compound corresponding to the acid number of the polyglycerol fatty acid ester mixture and/or at least equivalent to the amount of catalyst used additionally being added in the first extraction step, and the organic phase remaining after the extraction being freed from the organic solvent employed and the residual water content by distillation, preferably vacuum distillation or vacuum evaporation.

The organic chemical solvent or solvent mixture employed in the extraction treatment preferably has a water absorption capacity of less than 30% by weight, in particular less than 20% by weight (relative to 100 parts by weight of the organic chemical solvent or solvent mixture), and/or forms an azeotropic mixture with water during the distillation or in the gas phase.

One organic chemical solvent that has these properties is ethyl acetate, which is preferably employed in the extraction process as a water-saturated organic phase.

Further organic chemical solvents which can be used according to the invention include, inter alia, butanol and/or toluene.

In accordance with a preferred embodiment, the extraction is carried out in more than two steps, preferably in three steps.

The neutralization of the catalyst is preferably carried out according to the invention using sodium hydroxide, in particular using aqueous sodium hydroxide solution, the alkaline compound or solution being added to the organic chemical solvent or solvent mixture and/or the water phase in the first extraction step.

Other suitable neutralizing agents include alkali metal carbonates, preferably sodium carbonate and/or potassium carbonate, and/or a basic ion exchanger, which in each case are added to the organic chemical solvent or solvent mixture and/or the water phase in the first extraction step.

If the polyglycerol fatty acid ester mixture prepared according to the invention is allowed to stand for more than 0.5, preferably 1 to 10, hours before further processing and/or purification, unreacted contents of polyglycerol can optionally be precipitated and separated from the product mixture.

The constant quality of the final product, the defined composition of the ester mixture and the reproducibility of the reaction result in this process are particularly obtained by carrying out the reaction under controlled conditions of heating and simultaneous pressure reduction in the reaction mixture and also by exactly maintaining specific pressure and temperature ranges.

The process according to the invention can be carried out continuously under control of an appropriate temperature and pressure control program, or batchwise by stepwise heating and pressure reduction.

In this case, it was found as an advantageous embodiment of the process according to the invention to carry out the heating of the reaction mixture in the temperature range from 140° to 220° C., preferably 145° to 190° C., and the pressure reduction from 600 to 10 mbar, preferably from 500 to 20 mbar, for a time period of 2 to 6 hours, preferably 3 to 4 hours.

According to a further preferred embodiment of the process according to the invention, the heating of the reaction mixture in the temperature range from 140° to 220° C., preferably 145° to 190° C., is carried out stepwise in 3 to 6 steps, preferably 4 to 5 steps.

In corresponding manner, the reduction of the pressure from 600 to 10 mbar, preferably 500 to 20 mbar, can be carried out stepwise in a specific number of steps, preferably in 3 to 6 steps, in particular 4 to 5 steps.

The esterification reaction by the process according to the invention is carried out in the presence of a catalyst, preferably in the presence of an acidic compound containing sulfonic acid groups, such as, for example, dodecylbenzenesulfonic acid or other alkylbenzenesulfonic acids.

In accordance with one embodiment, this acidic catalyst is employed in combination with a second acidic compound having catalytic and reducing activity. A suitable compound in this respect is hypophosphorous acid.

According to a further advantageous embodiment of the process according to the invention, the reaction mixture is reacted in the presence of an inert gas atmosphere, preferably under nitrogen.

The present invention furthermore relates to polyglycerol fatty acid ester mixtures, liquid thickening agents having a skin-care action and oil/water emulsifiers having skin-care properties for use in creams or ointments, which are preferably prepared by the process according to the invention.

The polyglycerol fatty acid ester mixture has (relative to 100 parts by weight of the polyglycerol fatty acid ester mixture)
(A) a content of
  0.1 to 20% by weight of monoglycerol fatty acid ester,
  20 to 35% by weight of diglycerol fatty acid ester,
  30 to 40% by weight of triglycerol fatty acid ester, and
  49.9 to 5% by weight of tetra- and higher polyglycerol fatty acid esters,
the fatty acid component consisting of one or more fatty acids selected from the saturated $C_8$- to $C_{18}$-fatty acids having a content of 0 to 15% by weight of unsaturated fatty acids, and
(B) a degree of esterification of
  20 to 80% by weight of fatty acid monoesters, and
  80 to 20% by weight of fatty acid diesters containing
    0 to 15% by weight of tri- and higher esters,
and no or only small amounts (less than 5% by weight) of free polyglycerol being contained in the polyglycerol fatty acid ester mixture.

According to a preferred embodiment, the polyglycerol fatty acid ester mixture has (relative to 100 parts by weight of the polyglycerol fatty acid ester mixture)
(A) a content of
  6 to 16% by weight of monoglycerol fatty acid ester,
  23 to 33% by weight of diglycerol fatty acid ester,
  31 to 37% by weight of triglycerol fatty acid ester, and
  40 to 14% by weight of tetra- and higher polyglycerol fatty acid esters,
the fatty acid component consisting of one or more fatty acids selected from the saturated $C_8$- to $C_{18}$-fatty acids having a content of 0 to 10% by weight of unsaturated fatty acids, and
(B) a degree of esterification of
  30 to 70% by weight of fatty acid monoesters, and
  70 to 30% by weight of fatty acid diesters containing
    0.5 to 7% by weight of tri- and higher esters,
no or only small amounts (less than 2.5% by weight) of free polyglycerol being contained in the polyglycerol fatty acid ester mixture.

The liquid thickening agent having a skin-care action, prepared by the process according to the invention consists of or contains a polyglycerol fatty acid ester mixture which has (relative to 100 parts by weight of the polyglycerol fatty acid ester mixture)
(A) a content of
  0.1 to 20% by weight of monoglycerol fatty acid ester,
  20 to 35% by weight of diglycerol fatty acid ester,
  30 to 40% by weight of triglycerol fatty acid ester, and
  49.9 to 5% by weight of tetra- and higher polyglycerol fatty acid esters,
the fatty acid component consisting of one or more fatty acids selected from the saturated $C_8$- to $C_{18}$-fatty acids, preferably capric acid, and
(B) a degree of esterification of
  20 to 80% by weight of fatty acid monoesters, and
  80 to 20% by weight of fatty acid diesters containing
    0 to 15% by weight of tri- and higher esters,
no or only small amounts (less than 5% by weight) of free polyglycerol being contained in the polyglycerol fatty acid ester mixture.

A thickening agent of this type not only has skin-care action, but it can additionally be processed cold and can be easily metered due to its liquid state at room temperature, so that it can be incorporated in cosmetic or pharmaceutical formulations in a simple manner. The surprising actions of the thickening agent can in this case be traced back in particular to the use of capric acid as the fatty acid component, this fatty acid being employed in pure form without or only with trace amounts of unsaturated fatty acids.

According to a preferred embodiment, the liquid thickening agent having a skin-care action consists of a polyglycerol fatty acid ester mixture which has (relative to 100 parts by weight of the polyglycerol fatty acid ester mixture)

(A) a content of
  6 to 16% by weight of monoglycerol fatty acid ester,
  23 to 33% by weight of diglycerol fatty acid ester,
  31 to 37% by weight of triglycerol fatty acid ester, and
  40 to 14% by weight of tetra- and higher polyglycerol fatty acid esters, the fatty acid component consisting of one or more fatty acids selected from the saturated $C_8$- to $C_{18}$-fatty acids, preferably capric acid, and (B) a degree of esterification of
  30 to 70% by weight of fatty acid monoesters, and
  70 to 30% by weight of fatty acid diesters containing 0.5 to 7% by weight of tri- and higher esters, no or only small amounts (less than 2.5% by weight) of free polyglycerol being contained in the polyglycerol fatty acid ester mixture.

The oil/water emulsifier having skin-care properties for use in creams or ointments, prepared by the process according to the invention consists of or contains a polyglycerol fatty acid ester mixture which has (relative to 100 parts by weight of the polyglycerol fatty acid ester mixture)

A) a content of
  0.1 to 20% by weight of monoglycerol fatty acid ester,
  20 to 35% by weight of diglycerol fatty acid ester,
  30 to 40% by weight of triglycerol fatty acid ester, and
  49.9 to 5% by weight of tetra- and higher polyglycerol fatty acid esters, the fatty acid component consisting of one or more fatty acids selected from the saturated $C_8$- to $C_{18}$-fatty acids having a content of 0 to 15% by weight of unsaturated fatty acids, preferably coconut fatty acid, and (B) a degree of esterification of
  20 to 80% by weight of fatty acid monoesters, and
  80 to 20% by weight of fatty acid diesters containing 0 to 15% by weight of tri- and higher esters, no or only small amounts (less than 5% by weight) of free polyglycerol being contained in the polyglycerol fatty acid ester mixture.

The oil/water emulsifier according to the invention is outstandingly suitable for creams and ointments, since it has skin-care properties and causes a very pleasant skin sensation in topical formulations. The coconut fatty acid employed is a mixture of saturated and unsaturated fatty acids, where the content of unsaturated fatty acids can be between 0 and 15% by weight.

According to a preferred embodiment, the oil/water emulsifier having skin-care properties for use in creams or ointments consists of a polyglycerol fatty acid ester mixture which has (relative to 100 parts by weight of the polyglycerol fatty acid ester mixture)

(A) a content of
  6 to 16% by weight of monoglycerol fatty acid ester,
  23 to 33% by weight of diglycerol fatty acid ester,
  31 to 37% by weight of triglycerol fatty acid ester, and
  40 to 14% by weight of tetra- and higher polyglycerol fatty acid esters, the fatty acid component consisting of one or more fatty acids selected from the saturated $C_8$- to $C_{18}$-fatty acids having a content of 4 to 10% by weight of unsaturated fatty acids, preferably coconut fatty acid, and (B) a degree of esterification of
  30 to 70% by weight of fatty acid monoesters, and
  70 to 30% by weight of fatty acid diesters containing 0.5 to 7% by weight of tri- and higher esters, no or only small amounts (less than 2.5% by weight) of free polyglycerol being contained in the polyglycerol fatty acid ester mixture.

The invention furthermore relates to the use of the polyglycerol fatty acid ester mixture prepared by the process according to the invention as a solubilizing agent, thickening agent, oil-restoring agent and/or emulsifier in cosmetic, pharmaceutical or chemical preparations.

The polyglycerol fatty acid ester mixture according to the invention has many uses. It is preferably used for solubilizing and/or emulsifying ethereal oils and/or perfume oils. It is therefore outstandingly suitable for preparing bath additives, in particular bath oils or oil baths.

In addition, the polyglycerol fatty acid ester mixture prepared according to the invention can be used as a skin-care additive and/or detergent, cleaning agent or body cleansing agent, shampoo, shower gel or shower composition, foam bath composition, liquid hand-cleaning agent or hair shampoo, since at the same time it also has surface-active properties and, in addition to a mild cleaning action, certain additional properties, such as, for example, a oil-restoring effect and a pleasant skin sensation during and after the cleaning process, an improved flow behavior, and moreover, dermatological and toxicological acceptability.

Further areas of use for the polyglycerol fatty acid ester mixture according to the invention include foodstuffs and medicaments, ointments, pharmaceutical and cosmetic preparations of any type where the polyglycerol fatty acid ester mixture acts as a solubilizing and-/or thickening agent and/or emulsifier. Its many uses result, inter alia, from the fact that the polyglycerol fatty acid ester mixture according to the invention is, on the one hand, easily processable and, on the other hand, neutral or beneficial to the skin and body. Cosmetic preparations using the polyglycerol fatty acid ester mixture according to the invention impart an optimum caring sensation. When used on the skin, e.g. in cosmetic preparations, skin disinfectants, ointments, embrocations and the like, the polyglycerol fatty acid ester mixture according to the invention has a oil-restoring effect.

It was not to be expected that these properties and results could be achieved with the polyglycerol fatty acid ester mixture according to the invention and that moreover such requirements as those of dermatological activity and of toxicological acceptability are also fulfilled.

In addition, the polyglycerol fatty acid ester mixture according to the invention is especially suitable for industrial applications, preferably as an emulsifier in drilling oils or drilling fluids as well as lubricating oils, and also as a wetting and/or dispersing agent in industrial cleaning agents or as an emulsifier and/or dispersing agent in dye preparations, pigment dispersions, or preservatives for buildings, in particular protective coatings and glazes for wood.

The polyglycerol fatty acid ester mixture can be combined without difficulty in ready-to-use formulations with further additives or adjuvants. Electrolytes and/or further surfactants and also solvents and/or diluents can preferably additionally be employed in detergents, cleaning agents and/or body cleansing agents. In addition, the polyglycerol fatty acid ester mixture according to the invention can be used together with preservatives, perfuming compositions, colorants, pharmaceutically active compounds, pH adjusting compositions, complexing agents for masking metal ions, skin-care agents and/or thickening agents and other compounds such as colloids, disinfectants, fungicides, insecticides or bactericides, corrosion inhibitors, etc.

The following examples are intended to illustrate the invention in further detail without restricting its scope.

EXAMPLE 1

Preparation of Polyglycerol Cocoate

A mixture of 977 g (=4.16 moles) of polyglycerol (consisting of about 15% glycerol, about 25% diglycerol, about 31% triglycerol, about 17% tetraglycerol and about 12% higher oligomers), 878 g (=4.16 moles) of coconut fatty acid, 2.8 g of dodecylbenzenesulfonic acid, and 1.1 g of hypophosphorous acid was heated from 145° C. to a maximum of 165° C. at 500 to 20 mbar over the course of about 3 hours with stirring and simultaneous passage of inert gas in a 2-liter four-neck flask, which was provided with a stirrer, water separator, thermometer, and gas inlet tube. The water of reaction was continuously removed by distillation. Upon attaining an acid number of <2, the reaction mixture was cooled to about 65° to 70 ° C., and the unreacted polyglycerol content was removed as follows.

The reaction mixture was dissolved in ethyl acetate (half the amount by volume, saturated with water) and extracted with water in three steps. In the first step, an amount of sodium hydroxide solution corresponding to the acid number was added to the aqueous ethyl acetate. The total amount of water used for the extraction was about 87% by volume of the ester employed. After removal of the solvent by distillation, the total amount of extracted polyglycerol was about 611 g. The organic phase which remained after the extraction was evaporated in vacuo.

| Characterizing Data: | Ester Content Wt-%: |
|---|---|
| Acid No.: 2.5 mg KOH/g | Monoester: ≈25 |
| Saponification No.: 167.0 mg KOH/g | Diester: ≈65 |
| Viscosity @ 50° C.: 450 mPa.s | Higher esters: ≈10 |

EXAMPLE 2

Preparation of Polyglycerol Caprate

A mixture of 939 g (=4 moles) of polyglycerol (consisting of about 15% of glycerol, about 25% of diglycerol, about 31% of triglycerol, about 17% of tetraglycerol and about 12% of higher oligomers), 688 g (=4 moles) of capric acid, 2.8 g of dodecylbenzenesulfonic acid, and 1.1 g of hypophosphorous acid was heated from 145° C. to a maximum of 165° C. at 500 to 20 mbar over the course of about 3 hours with stirring and simultaneous passage of inert gas in a 2-liter four-neck flask provided with a stirrer, water separator, thermometer and gas inlet tube. The water of reaction was continuously removed by distillation. Upon attaining an acid number of <2, the reaction mixture was cooled to about 65° to 70° C., and the unreacted polyglycerol content was removed as follows.

The reaction mixture was dissolved in ethyl acetate (half the amount by volume, saturated with water) and extracted with water in three steps. In the first step, an amount of sodium hydroxide solution corresponding to the acid number was added to the aqueous ethyl acetate. The total amount of water used for the extraction was about 87% by volume of the ester employed. After removal of the solvent by distillation, the total amount of extracted polyglycerol was about 309 g. The organic phase which remained after the extraction was evaporated in vacuo.

| Characterizing Data: | Ester Content Wt-%: |
|---|---|
| Acid No.: 1.6 mg KOH/g | Monoester: ≈50 |
| Saponification No.: 174.8 mg KOH/g | Diester: ≈40 |
| Viscosity @ 20° C.: 4600 mPa.s | Higher esters: ≈10 |

EXAMPLE 3

Preparation of Polyglycerol Laurate

A mixture of 858 g (=3.65 moles) of polyglycerol (consisting of about 15% of glycerol, about 25% of diglycerol, about 31% of triglycerol, about 17% of tetraglycerol and about 12% of higher oligomers), 811 g (=4.06 moles) of lauric acid, 2.8 g of dodecylbenzenesulfonic acid, and 1.1 g of hypophosphorous acid was heated from 145° C. to a maximum of 165° C. at 500 to 20 mbar over the course of about 3 hours with stirring and simultaneous passage of inert gas in a 2-liter four-neck flask provided with a stirrer, water separator, thermometer and gas inlet tube. The water of reaction was continuously removed by distillation. Upon attaining an acid number of <2, the reaction mixture was cooled to about 60° to 65° C., and the unreacted polyglycerol content was removed as follows.

The reaction mixture was dissolved in ethyl acetate (half the amount by volume, saturated with water) and extracted with water in three steps. In the first step, an amount of sodium hydroxide solution corresponding to the acid number was added to the aqueous ethyl acetate. The total amount of water used for the extraction was about 87% by volume of the ester employed. After removal of the solvent by distillation, the total amount of extracted polyglycerol was about 253 g. The organic phase which remained after the extraction was evaporated in vacuo.

| Characterizing Data: | Ester Content wt-%: |
|---|---|
| Acid No.: 1.1 mg of KOH/g | Monoester: ≈35 |
| Saponification No.: 166.3 mg KOH/g | Diester: ≈55 |
| Viscosity @ 20° C.: 10,100 mPa.s | Higher esters: ≈10 |

EXAMPLE 4

Preparation of Polyglycerol Isostearate

A mixture of 470 g =2.0 mole of polyglycerol (consisting of about 15% of glycerol, about 25% of diglycerol, about 31% of triglycerol, about 17% of tetraglycerol and about 12% of higher oligomers), 1080 g=3.8 mole of isostearic acid, 2.8 g of dodecylbenzenesulfonic acid and 1.1 g of hypophosphorous acid was heated from 145° C. to a maximum of 170° C. at 500 to 20 mbar during the course of about 4 h with stirring and simultaneous passage of inert gas in a 2-liter four-neck flask which was provided with a stirrer, water separator, thermometer and gas inlet tube, the water of reaction being continuously removed by distillation. On attaining an acid number of <2, the reaction mixture was cooled down to about 60° to 65° C. and unreacted contents of polyglycerol are removed as follows: The reaction mixture was dissolved in ethyl acetate (half the amount by volume, saturated with water) and extracted with water in three steps. In the first step, an amount of sodium hydroxide solution corresponding to the acid number was added to the aqueous ethyl acetate. The total volume of water used for the extraction was about 50% of the volume of the ester. After removal of the solvent by distillation, the total amount of extracted polyglycerol was about 67 g. The organic phase which remained after the extraction was evaporated in vacuo.

Characterizing Data

Acid No. 1.5 mg KOH/g
Saponification No.: 153.6 mg KOH/g
Viscosity @25° C.: 5500 mPa.s

EXAMPLE 5

Preparation of Polyglycerol Isostearate

A mixture of 352 g (=1.5 moles) of polyglycerol (consisting of about 15% of glycerol, about 25% of diglycerol, about 31% of triglycerol, about 17% of tetraglycerol and about 12% of higher oligomers), 1108 g (=3.9 moles) of isostearic acid, 2.8 g of dodecylbenzenesulfonic acid, and 1.1 g of hypophosphorous acid was heated from 145° C. to a maximum of 190° C. at 500 to 20 mbar over the course of about 4 hours with stirring and simultaneous passage of inert gas in a 2-liter four-neck flask provided with a stirrer, water separator, thermometer and gas inlet tube. The water of reaction was continuously removed by distillation. Upon attaining an acid number of <2, the reaction mixture was cooled to about 60° to 65° C. Unreacted polyglycerol was not removed.

Characterizing Data

Acid No.: 2.2 mg KOH/g
Saponification No.: 157.4 mg KOH/g
Viscosity @25° C.: 2200 mPa.s Examples of Use of Polyglycerol Fatty Acid Ester Mixtures Prepared According to the Invention Example I. Oil/water skin cream containing the PGLC cocoate according to the invention as an oil/water emulsifier.

A composition was prepared comprising the following ingredients:
 1.5% polyglycerol cocoate (Prepn. Example 1)
 2.0% cetyl-stearyl alcohol
 9.1% glycerol mono/distearate
 4.0% cetearyl isononanoate (Cetial SN, Henkel)
 5.0% liquid paraffin GP, viscous
 1.6% calendula extract
 8.0% diglycerol
 0.12% polyacrylic acid (Carbopol 940, B. F. Goodrich)
 0.22% neutralizing agent
 0.05% preservative
 0.3% perfume
 68.11% water, completely demineralized The composition was a slightly oily, smooth, soft cream with very rapid absorption power and very good skin sensation. Stability at 20° C. and 40° C.: >2 months.

Example II. Standard hair shampoo containing PGLC caprate according to the invention as a thickener and skin-care additive. (Total surfactant content: 17%)

A composition was prepared comprising the following ingredients:
 50% sodium lauryl ether sulfate (28% strength)
 3% polyglycerol caprate (Prep. Example 2)
 2% sodium chloride
 0.05% preservative
 0.2% perfume
 44.75% water, completely demineralized Viscosity: 4000 mPa.s
Ross/Miles Foam number according to DIN 53902: (1 g/liter of detergent; 40° C.; distilled water)

|                | |
|----------------|---------|
| after 30 sec   | 200 mm  |
| after 3 min    | 195 mm  |
| after 5 min    | 195 mm. |

Example III. Body soap and hair shampoo which is mild to the skin containing PGLC caprate according to the invention as a thickener and skin-care additive. (Total surfactant content: 12%)

A composition was prepared comprising the following ingredients:
 21.8% Na lauryl ether sulfate, 28% strength
 2.0% polyglycerol caprate (Prepn. Example 2)
 6.7% alkylamidobetaine 30%
 5.0% disodium fatty alcohol polyglycol ether sulfosuccinate, 40% strength
 1.7% sodium chloride
 0.05% preservative
 0.3% perfume
 62.45% water, completely demineralized.

Viscosity: 4100 mPa.s.
Ross/Miles Foam number according to DIN 53902: (1 g/liter of detergent; 40° C.; distilled water)

|                | |
|----------------|---------|
| after 30 sec   | 195 mm  |
| after 3 min    | 190 mm  |
| after 5 min    | 185 mm. |

Example IV. Oil/water body lotion containing PGLC laurate according to the invention.

A composition was prepared comprising the following ingredients:
 3.5% polyglycerol laurate (Prepn. Example 3)
 7.0% caprylic/capric acid triglyceride (neutral oil)
 3.0% propylene glycol dicaprylate/dicaprate (Miglyol 840, Hüls AG)
 5.0% wheat germ oil
 0.21% polyacrylic acid (Carbopol 940, B. F. Goodrich)
 0.32% neutralizing agent
 0.05% preservative
 0.6% perfume
 80.32% water, completely demineralized The product was a moderately oily, viscous lotion with very rapid absorption power and a very pleasant skin sensation. Stability at 20° C. and 40° C.: >2 months.

Example V. Water/oil skin cream containing PGLC/isostearate according to the invention as a water/oil emulsifier. (Molar ratio: 1 mole PGLC: 2.5 moles isostearic acid)

A composition was prepared comprising the following ingredients:
- 2.5% polyglycerol isostearate (Prepn. Example 5)
- 3.5% decyl oleate (Cetiol V, Henkel)
- 3.0% dioctylcyclohexane (Cetiol S, Henkel)
- 3.5% liquid paraffin GP, viscous
- 0.7% magnesium stearate
- 0.3% aluminum stearate
- 4.0% diglycerol
- 0.3% magnesium heptahydrate
- 0.05% preservative
- 0.3% perfume
- 81.85% water, completely demineralized The product was a slightly oily, white, lustrous, soft cream with an unusually rapid absorption power into the skin for water/oil creams and an excellent skin sensation. Stability at 20° C. and 40° C.: >2 months.

Example VI. Skin-care Oil Bath

A composition was prepared comprising the following ingredients:
- 43% polyglycerol caprate (Prepn. Example 2)
- 42% rosemary oil
- 15% water, completely demineralized.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A polyglycerol fatty acid ester mixture prepared by reacting a polyglycerol with at least one fatty acid selected from the group consisting of saturated $C_8$- to $C_{18}$-fatty acids containing 0 to 15 wt % of unsaturated fatty acids at elevated temperature, said polyglycerol fatty acid ester mixture
(A) comprising:
   0.1 to 20 parts by weight monoglycerol fatty acid ester,
   20 to 35 parts by weight diglycerol fatty acid ester,
   30 to 40 parts by weight triglycerol fatty acid ester, and
   49.9 to 5 parts by weight tetra- and higher polyglycerol fatty acid esters,
for a total of 100 parts by weight;
(B) having a degree of esterification of
   20 to 80 wt % of fatty acid monoesters, and
   80 to 20 wt % of fatty acid diesters containing 0 to 15 wt % of tri- and higher esters, and
(C) containing 0 to less than 5 wt % free polyglycerol.

2. A composition according to claim 1, used as a liquid thickening agent having a skin-care action, wherein said at least one fatty acid is capric acid.

3. A composition according to claim 1, used in creams and ointments as an oil/water emulsifier having skin-care properties, wherein said at least one fatty acid is coconut fatty acid.

4. A polyglycerol fatty acid ester mixture according to claim 1, prepared by reacting a polyglycerol with at least one fatty acid selected from the group consisting of saturated $C_8$- to $C_{18}$-fatty acids containing 0 to 10 wt % of unsaturated fatty acids, said polyglycerol fatty acid ester mixture:
(A) comprising:
   6 to 16 parts by weight monoglycerol fatty acid ester,
   23 to 33 parts by weight diglycerol fatty acid ester,
   31 to 37 parts by weight triglycerol fatty acid ester, and
   40 to 14 parts by weight tetra- and higher polyglycerol fatty acid esters,
for a total of 100 parts by weight;
(B) having a degree of esterification of
   30 to 70 wt % of fatty acid monoesters, and
   70 to 30 wt % of fatty acid diesters containing 0.5 to 10 wt % of tri- and higher esters, and
(C) containing 0 to less than 2.5 wt % free polyglycerol.

5. A composition according to claim 4, for use as a liquid thickening agent having a skin-care action, wherein said at least one fatty acid is capric acid.

6. A composition according to claim 4, for use in creams and ointments as an oil/water emulsifier having skincare properties, wherein said at least one fatty acid contains from 4 to 10 wt % of unsaturated fatty acids.

7. A composition according to claim 6, wherein said at least one fatty acid is coconut fatty acid.

8. A process for preparing a polyglycerol fatty acid ester mixture from a $C_8$- to $C_{24}$-fatty acid and a polyglycerol mixture containing 0 to 5 wt % monoglycerol, 15 to 40 wt % diglycerol, 30 to 55 wt % triglycerol, 10 to 25 wt % tetraglycerol, and 0 to 30 wt % higher polyglycerols with acidic catalysis, said process comprising reacting a polyglycerol comprising (relative to 100 parts by weight of polyglycerol):
   0.1 to 20 wt % monoglycerol,
   20 to 35 wt % diglycerol,
   30 to 40 wt % triglycerol, and
   49.9 to 5 wt % tetra- and higher polyglycerols,
with at least one fatty acid selected from the group consisting of saturated $C_8$- to $C_{18}$-fatty acids, said at least one fatty acid containing from 0 to 15 wt % unsaturated fatty acids, in a molar ratio of polyglycerol to said at least one fatty acid of from 0.3:1.5 to 1.5:0.5, in the presence of at least one catalyst and at reduced pressure, said reacting step being carried out by:
   initially heating the fatty acid and polyglycerol mixture to a temperature of at least 140° C. and reducing the pressure to 600 mbar;
   subsequently heating the mixture in a temperature range from 140° to 220° C. under control of a temperature program and simultaneously reducing the pressure under control of a pressure program from 600 to 10 mbar;
   removing water of reaction by continuous distillation; and
   upon attaining an acid number of less than 3, cooling the resulting polyglycerol fatty acid ester mixture.

9. A process according to claim 8, wherein the molar ratio of said polyglycerol to said at least one fatty acid is from 0.5:1 to 1.2:1.

10. A process according to claim 8, wherein said catalyst is an acidic catalyst.

11. A process according to claim 8, wherein said reaction mixture is heated in said initial heating step to a temperature of at least 145° C., and the pressure is reduced in said initial pressure reduction step to at most 500 mbar.

12. A process according to claim 8, wherein said reaction mixture is subsequently heated in a temperature range from 145° to 190° C., and the pressure is subsequently reduced to a pressure in the range from 500 to 20 mbar.

13. A process according to claim 8, wherein said subsequent heating and pressure reducing steps under program control are effected stepwise.

14. A process according to claim 8, wherein said subsequent heating and pressure reducing steps under program control are effected continuously.

15. A process according to claim 8, further comprising purifying said cooled polyglycerol fatty acid ester mixture.

16. A process according to claim 8, wherein said polyglycerol comprises 6 to 16 wt % monoglycerol, 23 to 33 wt % diglycerol, 31 to 37 wt % triglycerol, and 40 to 14 wt % tetra- and higher polyglycerols, for a total of 100 wt %.

17. A process according to claim 8, wherein the resulting polyglycerol fatty acid ester mixture is cooled to a temperature in the range from 30° to 110 ° C.; said process further comprising freeing said cooled mixture from unreacted polyglycerol by treating said cooled mixture with an organic solvent, thereafter extracting the solvent-treated mixture with water in at least one extraction step, an amount of a basic substance at least equivalent to the amount of acidic catalyst used in the reacting step being added to the water used in a first of said at least one extraction step, and removing said organic solvent and residual water from the extracted, solvent-treated mixture.

18. A process according to claim 17, wherein the resulting polyglycerol fatty acid ester mixture is cooled to a temperature in the range from 60° to 80 ° C.

19. A process according to claim 17, wherein said amount of basic substance added to the first of said at least one extraction step is equivalent to the acid number of the polyglycerol fatty acid ester mixture.

20. A process according to claim 17, wherein said organic solvent and residual water are removed from the extracted, solvent-treated mixture by vacuum evaporation.

21. A process according to claim 17, wherein said organic solvent comprises a mixture of organic solvents.

22. A process according to claim 17, wherein said organic solvent has a water absorption capacity of less than 30 parts by weight water per 100 parts by weight solvent.

23. A process according to claim 22, wherein said organic solvent has a water absorption capacity of less than 20 parts by weight water per 100 parts by weight solvent.

24. A process according to claim 17, wherein said organic solvent forms an azeotropic mixture with water.

25. A process according to claim 17, wherein said organic solvent comprises ethyl acetate.

26. A process according to claim 25, wherein said solvent is water-saturated ethyl acetate.

27. A process according to claim 17, wherein the solvent-treated mixture is extracted with water in three extracting steps.

28. A process according to claim 17, wherein said basic substance is selected from the group consisting of alkali metal hydroxides, alkali metal carbonates, and basic ion exchangers.

29. A process according to claim 28, wherein said basic substance is an aqueous sodium hydroxide solution.

30. A process according to claim 28, wherein said basic substance comprises sodium carbonate or potassium carbonate.

31. A process according to claim 17, further comprising allowing said cooled polyglycerol fatty acid ester mixture to stand for at least one-half hour and separating any precipitated material before treating the cooled mixture to remove unreacted polyglycerol.

32. A process according to claim 31, wherein said cooled polyglycerol fatty acid ester mixture is allowed to stand for from 1 to 10 hours.

33. A process according to claim 8, wherein said subsequent heating and pressure reducing steps are carried out for from 2 to 6 hours.

34. A process according to claim 33, wherein said subsequent heating and pressure reducing steps are carried out for from 3 to 4 hours.

35. A process according to claim 13, wherein said subsequent heating step is carried out stepwise in from 3 to 6 steps.

36. A process according to claim 13, wherein said subsequent pressure reducing step is carried out stepwise in from 3 to 6 steps.

37. A process according to claim 13, wherein said subsequent heating step is carried out stepwise in from 4 to 5 steps, and said subsequent pressure reducing step is carried out stepwise in from 4 to 5 steps.

38. A process according claim 10, wherein said acidic catalyst is employed in combination with an acidic reducing compound.

39. A process according to claim 38, wherein said acidic catalyst is a compound containing a sulfonic acid group, and said acidic reducing compound is hypophosphorous acid.

40. A process according to claim 8, wherein said reacting step is carried out under an inert gas atmosphere.

41. A process according to claim 40, wherein said reacting step is carried out under a nitrogen atmosphere.

* * * * *